United States Patent [19]

Chang

[11] 4,376,210

[45] Mar. 8, 1983

[54] VINYL POLYSILOXANE POLYMERS RELEASE COMPOSITIONS AND METHODS

[75] Inventor: Mike S. H. Chang, Danbury, Conn.

[73] Assignee: Pitney Bowes Inc., Stamford, Conn.

[21] Appl. No.: 230,789

[22] Filed: Feb. 2, 1981

[51] Int. Cl.$^3$ ................................................ C07F 7/08
[52] U.S. Cl. ............................... 556/450; 204/159.13; 556/459
[58] Field of Search ............................... 556/450, 459

[56] References Cited

U.S. PATENT DOCUMENTS

| | | | |
|---|---|---|---|
| 3,037,962 | 6/1962 | Hartung et al. | 556/459 X |
| 3,155,634 | 11/1964 | Pike | 556/459 X |
| 3,843,601 | 10/1974 | Bruner | 556/459 X |
| 3,939,195 | 2/1976 | Zücking et al. | 556/459 |
| 4,008,346 | 2/1977 | Moeller | 556/450 X |
| 4,052,529 | 10/1977 | Bokerman et al. | 204/159.13 X |
| 4,064,027 | 12/1977 | Gant | 204/159.13 |
| 4,066,594 | 1/1978 | Moeller | 556/459 X |

OTHER PUBLICATIONS

Noll, "Chemistry & Technology of Silicones", *Academic Press,* N.Y. (1968), p. 196.

*Primary Examiner*—Paul F. Shaver
*Attorney, Agent, or Firm*—Melvin J. Scolnick; Albert Scribner; David E. Pitchenik

[57] ABSTRACT

Novel radiation-curable, liquid vinyl organosilicon polymers and coating compositions which are free of volatile solvent(s) and which are adapted to be applied to a substrate and cured rapidly by exposure to radiation to form release coatings having good release properties with respect to adhesives, and methods for producing such polymers and compositions and for applying and curing such release coatings.

5 Claims, No Drawings

VINYL POLYSILOXANE POLYMERS RELEASE COMPOSITIONS AND METHODS

BACKGROUND OF THE INVENTION

Release coating compositions are well-known in the art and are used extensively to coat substrates such as paper to provide release surfaces to which adhesive elements, such as labels or tapes can be adhered and from which said adhesive elements can be peeled or separated without damage to the adhesive or to the release surface or to the substrate. The release substrates and adhesive elements are united in order to prevent the adhesive elements, such as adhesive labels, adhesive tapes, adhesive floor tiles, or the like, from adhering to each other or to other surfaces from which they cannot be separated without tearing or breaking of the substrate or damage to the adhesive layer. The adhesive element-release substrate unit can be shipped, stored and handled without damage to the sticky adhesive layer, and they can be separated easily and cleanly by the ultimate user to permit the adhesive element to be permanently bonded to another surface.

Release coating compositions are known which are based upon curable organosilicon resins. Most commonly, such known compositions contain volatile organic solvents and are dried and cured by means of heating to elevated temperatures to evaporate the solvents and cure the organosilicon resins.

In order to reduce the cost and pollution inherent in the use of organic solvents, it has been proposed to use liquid vinyl containing organosilicon compositions which require no volatile solvent to form release coatings which are thermally-cured at elevated temperatures—reference is made to U.S. Pat. No. 4,216,252. Such coatings require relatively long dwell times and/or relatively hot ovens in order to produce a satisfactory cure of the release coatings, resulting in a waste of energy and/or a reduction in the line speed of the coating and curing operation.

It is also known to produce liquid vinyl organosilicon release compositions which do not require the presence of volatile organic solvents, and which are curable by means of exposure to radiation in the absence of applied heat. Reference is made to U.S. Pat. No. 4,052,529 which involves the use of siloxanes containing mercapto groups. Such release coatings are highly objectionable because of their bad odor. Moreover, they have slow curing rates and produce release coatings which are not suitable for use with strong adhesives. Reference is also made to U.S. Pat. No. 4,064,027 which relates to similar vinyl siloxane compositions which also have slow curing rates and unsatisfactory release properties for strong adhesives.

SUMMARY OF THE INVENTION

The present invention relates to the discovery of novel liquid vinyl polysiloxane polymers and to novel liquid, radiation-curable compositions comprising such vinyl siloxane polymers, a liquid polymethylhydro siloxane polymer (hereafter, PMHS) and a photosensitizer, which compositions are adapted to be coated in the absence of volatile solvents and cured at high speed under exposure to radiation, such as ultraviolet or electron beam, to form release coatings having excellent release properties even with respect to strong or so-called "aggressive" adhesives.

The essential novelty of the present invention resides in the novel liquid vinyl siloxane polymers which, unlike prior-known liquid vinyl siloxane polymers, provide coating compositions which can be cured rapidly under exposure to radiation to form dry release coatings having excellent release properties even with respect to strong adhesives, as discussed above.

The novel liquid vinyl siloxane polymers of the present invention have the basic structure:

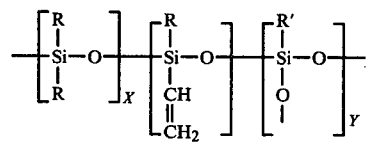

... wherein X and Y are numbers larger than 0. Preferably, Y is a number selected from a range of greater than 0 to about 10, more preferably 0.01 to 5 and most preferably 0.05 to 1, each R is the same or different monovalent hydrocarbon radicals selected from the group of $C_1$ to $C_4$ alkyl groups, cyclohexyl groups and phenyl groups and R' can be a R group or an oxygen radical, i.e., —O—. Such vinyl polymers may be prepared by reacting known starting materials such as dimethyl dichlorosilane, vinyl methyl dichlorosilane and tetrachlorosilane or trichloromethylsilane in suitable proportions under hydrolysis conditions which result in the evolution of hydrogen chloride. Generally, the formed liquid polymer is a light syrup which is suitable for use according to the present invention. The following example illustrates a preferred embodiment:

EXAMPLE 1

125 gms. of vinyl methyl dichlorosilane, 7.5 gms of tetrachlorosilane and 375 gms of dimethyl dichlorosilane are mixed in a one liter, 2-necked round bottom flask equipped with a dropping funnel and a condenser which is connected to a gas trap.

65 ml. of distilled water is added at a rate of about 3 to 4 ml per minute and the mixture is maintained at room temperature for about 4 hours to evolve hydrogen chloride gas. Thereafter, another 65 ml of the water is added at the same rate and mixing is continued until no more HCl gas is evolved, which takes about two hours.

The reaction mixture separates into two layers and the bottom aqueous layer is removed by a pipette or aspirator.

The remaining silicone layer is washed with 100 ml of 10% NaCl solution and the mixture is stirred vigorously until it is neutral. Two or three washings may be required.

Finally, the neutral silicone layer is dried over anhydrous magnesium sulfate for an hour or more and filtered. The yield is about 218 gms (75% of theoretical). The basic formula of the resultant liquid vinyl siloxane polymer is believed to be:

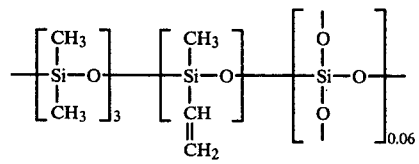

The formed polymer has a viscosity of between about 60 and 250 centipoises.

The following examples illustrate the preparation of radiation-curable coating compositions according to embodiments of the present invention.

EXAMPLE 2

5 gms of liquid vinyl siloxane polymer produced according to Example 1 are mixed with 5 gms of polymethylhydro siloxane (PMHS) and 0.5 gms of benzoin methyl ether photosensitizer available from Stauffer Chemical Co. under the registered trademark "Vi-cure-10". The siloxane components have the viscosity of light syrup and the viscosity of the mixture is about 60 centipoises which is good for thin coatings.

EXAMPLE 3

The procedure of Example 2 was followed exactly except for the substitution of 0.25 gm of benzophenone and 0.25 gm of dimethylethanol amine as a photosensitizer in place of the benzoin methyl ether of Example 2. The viscosity of the mixture is 60 centipoises but the composition is less stable than that of Example 2 and thickens so that the viscosity increases to about 225 centipoises after about 20 hours.

The compositions of Examples 1 and 2 are applied as a thin layer having a weight of about 0.5 lb/ream on semi-bleached paper substrates, and are cured in air by passing the coated substrates in a single pass through a QC Processor of Pittsburg Plate Glass Co. under the following conditions:

| Web speed | 200 ft/min. |
|---|---|
| Lamp #1 | 300 Watt/inch |
| Lamp #2 | 250 Watt/inch |

The cured release-coated paper substrates showed no sign of damage or warpage and, therefore, remoisturizing, as required in thermal-curing processes, is not necessary.

The release coated papers of Examples 2 and 3 were tested for release force and subsequent adhesion values and were found to have release forces of about 30 gm/in and about 50 gm/in, respectively, compared to a control release-coated paper which has a commercially-desired release force of about 10 to about 350 gm/in. The subsequent adhesion values were found to be about 2.7 lb/in. and 2.8 lb/in., respectively, compared to the control release-coated paper which has a commercially-desired adhesion value of 2.7 lb/in. Thus the release coatings of Examples 2 and 3 are highly satisfactory for commercial use.

While the applied weight of the release compositions of Examples 2 and 3 was about 0.5 lb/ream, it appears that lighter coat weights, such as about 0.3 lb/ream are also suitable. Also heavier coat weights such as about 1.5 lb/ream or more are also suitable, where required.

The speed at which the present release coatings are cured will depend upon the weight or thickness of the applied release coatings and the strength and proximity of the applied radiation, as will be clear to those skilled in the art. Generally, the present coatings can be cured at speeds up to about 250 feet/minute but preferably a speed of about 200 feet/minute is not exceeded in order to insure complete cure of the coating, particularly in the case of thicker coatings. Lower speeds, such as about 50 feet/minute can be used where speed is not important.

Another important feature of the novel release compositions of the present invention is their stability or pot life. While other known radiation-curable release compositions have a pot life of only about 4 hours, i.e., their viscosity increases so rapidly that they are no longer coatable after about four hours, the composition of Example 2 shows no increase in viscosity after 48 hours and the composition of Example 3 has its viscosity increase from 60 cps to 180 cps after 8 hours and to 225 cps after 20 hours, at which viscosity it is still coatable as a thin coating.

As discussed supra, the preparation of the novel liquid vinyl siloxane polymers of the present invention can be carried out in conventional manner using known starting materials in predetermined critical amounts which preferably comprise about one part by weight of a vinyl silicone component, more than one part by weight of a di-alkyl silicone component and less than about 0.1 part by weight of a tetrachlorosilane.

The liquid vinyl siloxane polymer is stable, per se, but reacts with the polymethylhydro siloxane in the presence of the photosensitizer under exposure to ultraviolet or electron beam radiation. The PMHS functions as a cross-linking agent with the vinyl groups of the siloxane polymer, and has the structure of functional repeating unit:

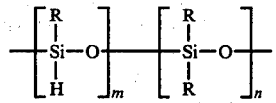

... in which R is a mono-valent hydrocarbon radical selected from the group consisting of $C_1$ to $C_4$ alkyl groups, cyclohexyl groups and phenyl groups; m is a number larger than 1, and n is a number equal to or greater than 0. The compound can be end-capped with trimethyl silyl groups, as known in the art. Preferably, n is equal to 0. The viscosity of the PMHS preferably is within the range of 2 to 1000 centistokes, more preferably between 20 and 100 centistokes and most preferably between about 30 and 50 centistokes.

While conventional photosensitizers may be used in the present compositions, the preferred materials are benzoin methyl ether and benophenone/dimethyl ethanol amine systems. Benzoin methyl ether is the most preferred photosensitizer.

The present release compositions preferably have a viscosity between 60 and 250 centipoises in order to be coatable as thin layers· without the need for volatile solvents. Generally, they comprise about 1 part by weight of the vinyl siloxane polymer, from about 0.8 to 1.2 part by weight of the polymethylhydro siloxane (PMHS) and from about 0.08 to 0.12 part by weight of one or more photosensitizers.

Variations and modifications of the present invention will be apparent to those skilled in the art within the scope of the present claims.

We claim:

1. Liquid vinyl polysiloxane polymer having the moiety structure:

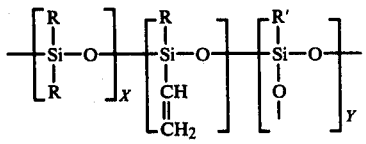

... wherein X is a number greater than 1; Y is a number selected from a range of greater than 0 and up to about 10; R is the same or different monovalent hydrocarbon radicals selected from the group consisting of $C_1$ to $C_4$ alkyl groups, cyclohexyl groups and phenyl groups; and R' is a R group or an oxygen radical.

2. A polymer according to claim 1 in which each R radical is a methyl group, X equals about 3 and Y equals about 0.06.

3. A polymer according to claim 1 or claim 2 having a viscosity between about 60 and 250 centipoises.

4. Method for producing the liquid vinyl polysiloxane polymer of claim 1 comprising the step of reacting more than about one part by weight of a di-alkyl dichlorosilane, about one part by weight of a vinyl dichlorosilane and less than about 0.1 part by weight of polychlorosilane under hydrolysis conditions.

5. Method according to claim 4 comprising the step of reacting more than about one part by weight of dimethyl dichlorosilane, about one part by weight of vinyl methyl dichlorosilane and less than about 0.1 part by weight of tetrachlorosilane under hydrolysis conditions.

* * * * *